United States Patent [19]

Weissman

[11] Patent Number: 4,854,871
[45] Date of Patent: Aug. 8, 1989

[54] METHOD AND APPARATUS FOR PROVIDING A LEVEL SURFACE ON A TOOTH ROOT

[75] Inventor: Bernard Weissman, New York, N.Y.

[73] Assignee: IPCO Corporation, White Plains, N.Y.

[21] Appl. No.: 123,747

[22] Filed: Nov. 23, 1987

[51] Int. Cl.⁴ ............................................. A61C 3/06
[52] U.S. Cl. ................................................ 433/166
[58] Field of Search ............... 433/221, 215, 225, 49, 433/165, 166; 15/206 R, 209 R, 210, 241 US

[56] References Cited

U.S. PATENT DOCUMENTS

| | | | |
|---|---|---|---|
| 1,200,921 | 10/1916 | Chester | 433/165 |
| 1,499,970 | 7/1924 | Bush | 433/165 |
| 1,734,548 | 11/1929 | Wacker | 51/241 VS |
| 2,453,696 | 11/1948 | Brooks | 433/102 |
| 2,748,483 | 6/1956 | Hoffmeister | 433/166 |
| 2,978,846 | 4/1961 | Barron | 51/206 R |
| 4,708,655 | 11/1987 | Weissman | 433/225 |

Primary Examiner—Robert Peshock
Attorney, Agent, or Firm—Helfgott & Karas

[57] ABSTRACT

A method and apparatus for forming a counterbored channel into the top surface of a tooth root in preparation for receiving a dental post and core during the fabrication of a superstructure on the tooth root. A dental tool is utilized for forming a counterbored recess around the mouth of a pre-drilled central bore. A dental jig having an enlarged flange which snugly fits into the counterbored channel is then used to form ancillary bores to provide a contoured aperture which will receive a correspondingly contoured post. The dental tool is then used to make similar counterbored recesses around the ancillary bores whereby the composite of the counterbored recesses forms a substantial oval channel wherein the core can suitably sit on a level surface perpendicular to the post without the necessity of leveling off the entire upper surface of the tooth root.

27 Claims, 5 Drawing Sheets

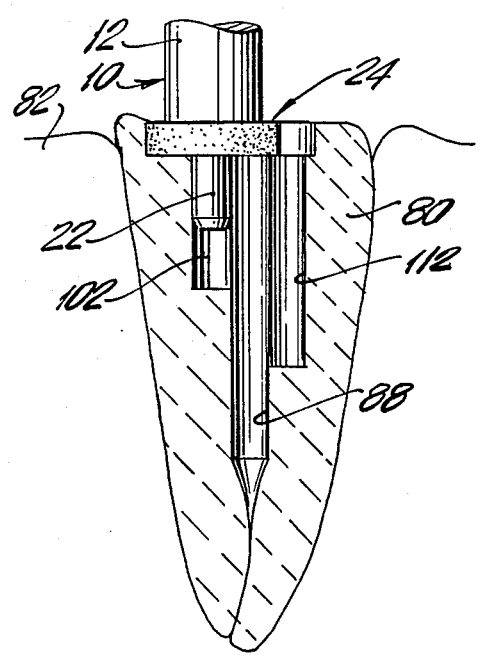
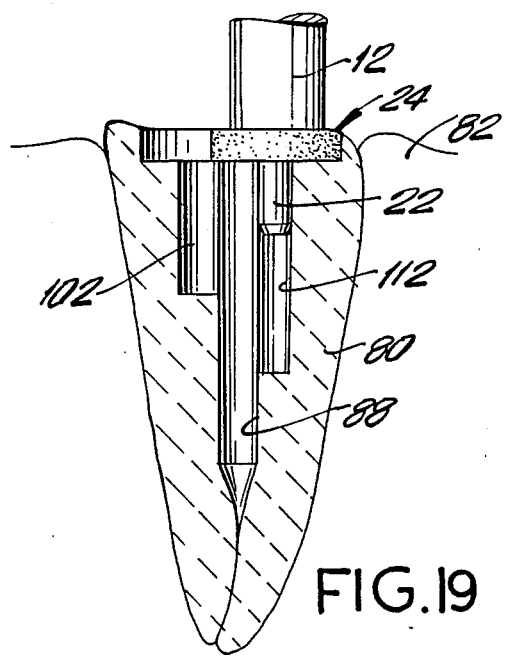
FIG.18　　FIG.19
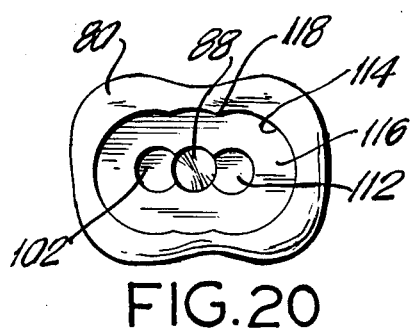
FIG.20
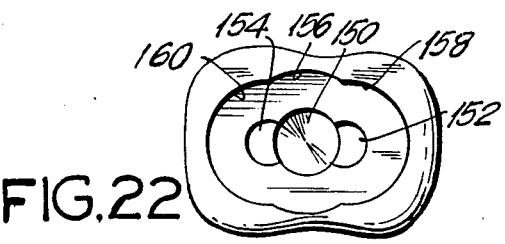
FIG.22
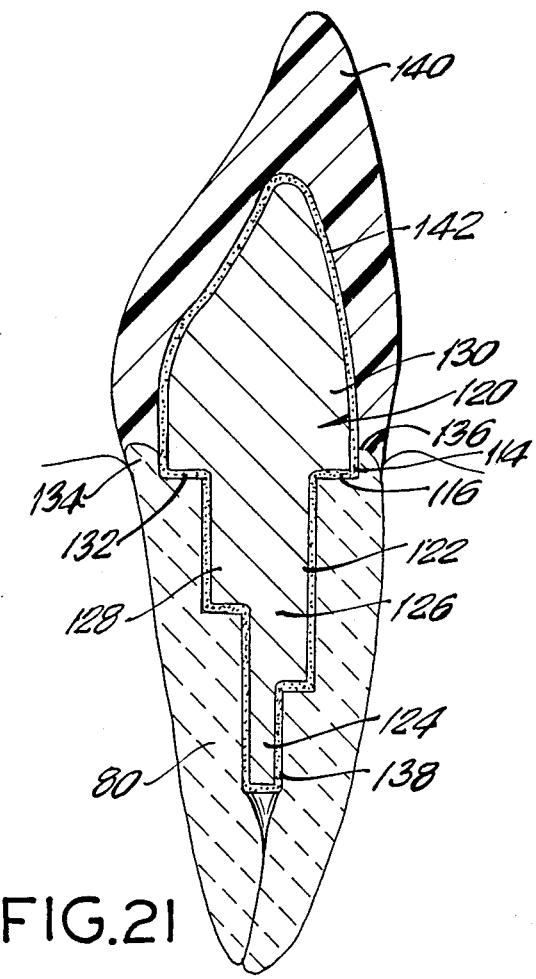
FIG.21

METHOD AND APPARATUS FOR PROVIDING A LEVEL SURFACE ON A TOOTH ROOT

BACKGROUND OF THE INVENTION

This invention relates to dental restoration systems, and more particularly to a method and apparatus for providing on a tooth root a level surface of a contour corresponding to the shape of the mouth of the root canal for thereby facilitating the installation of a post and core during the fabrication of a superstructure on the tooth root.

In the restoratin of devitalized dentition, a post and core is generally utilized for retaining a crown onto a tooth root. Typically, the tooth root is initially prepared by drilling a desired depth and diameter into the apical canal to provide an enlarged central bore for receiving a dental post. The dental post is then inserted and cemented in the bore. An appropriate core is built up on an upper portion of the dental post, and finally dental restorative material is used to fabricate the superstructure in the form of a crown on the core.

Since the actual canal in the tooth root tends to flare outwardly at its occlusal surface, the mouth of the canal at that surface of the tooth root tends to approach an oval shape. The enlarged central bore drilled into the tooth root, on the other hand, is generally circular in shape, and likewise the dental post is also circular in shape. Consequently, at the upper end, the dental post will not be securely retained in the tooth and will tend to laterally shift. While it would be possible to drill the central bore large enough to encompass the entire oval shape at the flared upper mouth, this would tend to destroy healthy dentition in the lower tooth and weaken the existing tooth root.

As a solution to this problem, U.S. Pat. No. 4,600,292, entitled "Contoured Dental Post" by the same inventor of the present application, describes a dental post which includes an elongated cylindrical pin provided with at least one radially projecting rib extending longitudinally along at least a portion of the length of the pin. Preferably, a pair of opposing ribs are utilized. The central cylindrical pin with the pair of diametrically opposed projecting ribs, approximates the oval shape of the mouth of the canal in the tooth root into which a correspondingly shaped bore can be formed for receiving the post. The side ribs project only partway down the length of the center pin to avoid the necessity of excessive drilling and destruction of healthy dentition. In order to provide an oriented insertion of the post, one rib is shorter than the other. To facilitate formation of an appropriate bore for receiving the contoured dental post, the aforementioned U.S. Patent also describes a dental drill jig for contouring the central bore in the tooth root into an approximate oval shape at the upper end of the bore in order to accommodate the contoured dental post. The dental jig includes a head having a stepped configuration. An elongated shaft depends from the center of the head block for insertion into the pre-drilled central bore formed into the tooth root. A pair of offset apertures are provided through the head block of the jig which extend into the shaft along opposing sides thereof. The distance from the top portion of each section of the stepped head to the lower distal end of the offset apertures in the shaft are substantially equal so that a single drill bit can be utilized to drill two ancillary bores into the tooth root. In this manner, the pair of ancillary bores are formed on either side of the central bore, contiguous with the central bore. One of the ancillary bores penetrates further into the depth of the tooth root than the other. The shape of the resulting aperture in the tooth root correspondingly receives the contoured dental post.

The aforementioned dental post and jig have been commerically incorporated into a dental post system referred to as the Triax TM, which is marketed by the Whaleadent International Division of IPCO Corporation.

While such system has been most successful, it is appropriate to have a level surface on the tooth root on which the dental jig can be positioned. In order to achieve such level surface, the tooth root is intially prepared by cutting it down below the damaged portion to provide the flat surface needed. In many instances, however, by cutting the tooth down to such level surface on which the dental jig can be placed, healthy dentition is destroyed which could otherwise be retained.

Likewise, in order to provide a suitable base upon which the dental core will sit, there is likewise needed a level portion at the occlusal surface of the tooth root. This is also achieved by leveling off the tooth root to provide a suitable planar surface. However, again, healthy dentition could be destroyed which could otherwise be retained and incorporated within the dental restoration built upon the tooth root.

SUMMARY OF THE INVENTION

Accordingly, it is an object of the present invention to provide an improved method and apparatus useful in the formation of a level surface at the occlusal surface of a tooth root.

Another object of the present invention is to provide a dental tool for leveling at least a portion of a tooth root.

Still another object of the present invention is to provide a dental tooth which can be used to provide a level surface on a tooth root perpendicular to a central predrilled bore in the tooth root.

Still a further object of the present invention is to provide a dental tool for providing a level dental surface approximating the oval shape of the mouth of the canal at the upper end of a dental root, while avoiding leveling the entire upper surface of the tooth root.

Yet another object of the present invention is to provide a dental tool for providing an oval recessed planar surface at the upper end of a tooth root for receiving the base of a dental core.

A further object of the present invention is to provide a dental jig having a flange which matingly sits into a level recessed surface on a tooth root, which jig is used in providing a contoured bore in a tooth root upon which a dental restoration is to be fabricated.

Yet a further object of the present invention is to provide a method of preparing a tooth root for receiving a post and core, by forming a substantially oval shaped level surface at the occlusal surface of the tooth root which receives the bottom of a dental core.

Another object of the present invention is to provide a dental tool for providing a recessed level seat at the occulsal surface of a tooth root in which a dental jig can snugly fit and wherein the dental jig is used for then providing a contoured bore in the tooth root upon which a dental restoration is to be fabricated.

Briefly, in accordance with the present invention, there is provided a dental tool for leveling at least a portion of the surface of a tooth root. The tooth root having a pre-drilled central bore. The bore is to be used for receiving a post and core during the fabrication of a superstructure on the tooth root. The dental tool includes an elongated shank. At the upper end of the shank is a suitable coupling arrangement for securement of the dental tool into a rotating apparatus. A cylindrical stem depends from an opposing end of the shank and is suitable for insertion into the predrilled bore. An enlarged annular collar intermediate the stem and shank has an undersurface facing the stem and a peripheral outer surface. Abrasive material is provided on the undersurface and the peripheral outer surface. In this manner, with the stem inserted into the tooth bore, rotation of the dental tool by means of the rotating apparatus will provide a level bottomed counterbore at the mouth of the bore.

In an embodiment of the invention, the undersurface is perpendicular to the stem whereby the bottom wall of the counterbore will be perpendicular to the axis of the post to be inserted into the central bore.

The present invention further contemplates a dental jig for use in making ancillary bores in the tooth root to provide a contoured aperture in the tooth root which approximate the oval shape of the mouth of the canal in the tooth root. The jig includes a head block with a cylindrical stem depending from the head block. The cylindrical stem is available for insertion into the pre-drilled central bore in the tooth root. A projecting flange interconnects the stem and the head block. The flange can seat snugly in the counterbore formed at the mouth of the central bore. A pair of spaced apart apertures parallel to the stem extends through the head block, the flange, and along at least a portion of the stem. Rotation of drill bits into the apertures forms the ancillary bores in the tooth root contiguous with and flanking the pre-drilled central bore to approximate the oval shape at the mouth of the canal.

In an embodiment of the invention, the dental tool can then be inserted into each of the ancillary bores to enlarge the center counterbore at the upper end of the tooth root by providing ancillary counterbore recesses at the mouths of the ancillary bores with the ancillary counterbored portions merging into the central counterbore portion to thereby provide an approximately oval shaped channel at the upper end of the tooth root. Such shape is suitable for receiving the bottom of a core upon insertion of a post and core on the tooth root.

It should be appreciated, that by forming a level recessed surface, and preferably one that is perpendicular to the central core axis, it is no longer necessary to completely level off the entire top surface of the tooth root. In this way, healthy dentition can be retained as a retention wall about the periphery of the channel to provide additional strength at the junction of the core and the tooth root.

The aforementioned objects, features and advanatages of the present invention will, in part, be pointed out with particularity and will, in part, become obvious from the following more detailed description of the present invention, taken in conjunction with the accompanying drawings, which form an integral part thereof.

BRIEF DESCRIPTION OF THE DRAWINGS

FIG. 18 shows a view similar to that shown in FIG. 16 with insertion of the dental tool of FIG. 1 into an ancillary bore to contour the level channel by forming a counterbored recess at the mouth of the ancillary bore;

FIG. 19 is a view similar to that shown in FIG. 18 and showing the formation of a counterbored recess at the mouth of the other ancillary bore;

FIG. 20 is a top view of the resultant tooth root showing the channel approximating the oval shape in the top of the tooth root;

FIG. 21 shows the final tooth including the post and core seated in the contoured bore in the tooth root and the contoured channel in the surface of the tooth root as well as the dental crown positioned and secured in place, and FIG. 22 is a view similar to that shown in FIG. 20, showing other sizes which can be used, and specifically where the center bore is larger than the side ancillary bores.

In the various figures of the drawings, like reference characters designate like parts.

DESCRIPTION OF THE PREFERRED EMBODIMENTS

In the formation of a superstructure on a tooth root, it is desirable to have a level surface on which a core can be positioned and, especially when utilizing a dental jig as described in the aforementioned U.S. Pat. No. 4,600,392, it is preferable to have a level surface on which the jig can sit. In order to avoid complete leveling of the upper surface of the tooth root, the dental tool of FIGS. 1-3 can be utilized.

Figure 1:
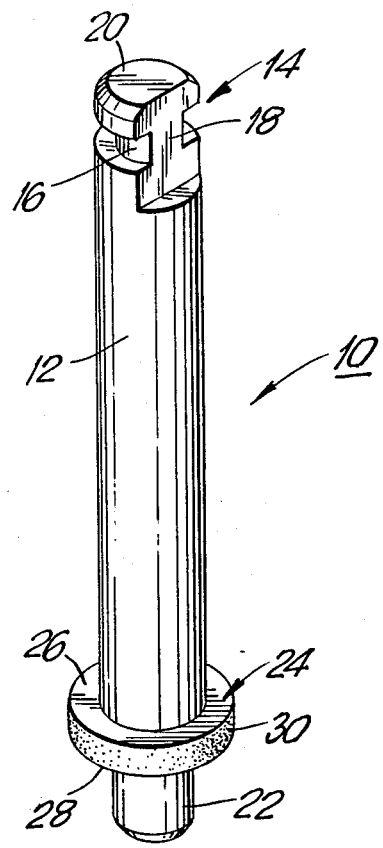
FIG. 1 is a perspective view of a dental tool for providing a counterbored recess in the occlusal surface of a tooth root, in accordance with the present invention.
Figure 3:
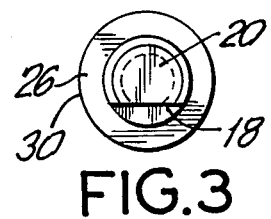
FIG. 3 is a top view of the dental tool shown in FIG. 2, and showing a coupling arrangement for insertion of the tool into a rotating apparatus.
Figure 2:
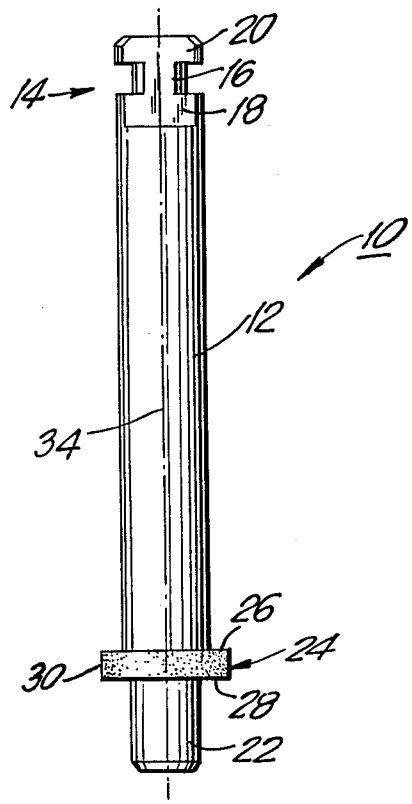
FIG. 2 is a side view of the dental tool shown in FIG. 1.

Referring to FIGS. 1-3, there is shown generally a dental tool 10 including a substantially clyindrical elongated shank portion 12. The upper end of the shank includes a coupling arrangement 14 for insertion into a dental hand piece which can drivingly rotate the dental tool 10. The usual coupling arrangement includes an undercut neck portion 16 sapced along the length of the shank and a flat face 18 on one side thereof. The coupling arrangement provides for an upper flat head 20 which can be locked into the dental handpiece. The coupling arrangement is well known in the art and is standard for interconnecting drills, and the like, into a rotating dental handpiece for drivingly rotating of the drill.

At the opposing end of the shank, there is provided a substantially clyindrical stem 22 depending from the tool. Interspersed between the stem 22 and the shank portion 12 is an enlarged annular flange 24. The flange includes an upper flat surface 26 and a lower flat surface 28 with a substantially cylindrical outer peripheral surface 30 therebetween. The undersurface 28 and the peripheral outer surface 24 include abrading or cutting material. Hereinafter, the term abrading will be used to denote all forms of cutting, grinding, etc. By way of example, the surface can be diamond plate, having a medium micron range of between 80 and 100, U.S. Standard Grade No. 90. In the emdbodiment as shown, the undersurface 28 is perpendicular to the central axis 34 of the dental tool whereby the portion cut by the undersurface will be perpendicular to the central axis of the bore in which the stem 22 is inserted.

Figure 4:
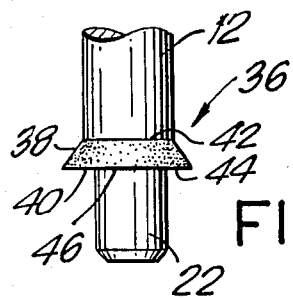
FIG. 4 is a partial side view of an alternate embodiment showing a different configuration of the flanged cutting edge.

As shown in FIG. 4, an alternate type of abrading flange 36 can be provided between the stem portion 22 and the shank portion 12. In this case, the flange 36 has an outer frustroconical peripheral shape 38 between its undersurface 40 and its upper edge 42. The angle is such that the upper edge 42 corresponds in diameter to the diameter of the shank 12. Abrading material 44 can be provided on the undersurface 40 and can wrap around the lip to cover at least a portion at the lower edge 46 of the frustroconical side 38. Although in the prior art secondary drills were used to provide a counterbore to a drilled bore, none of these tools had any abrading surface along the outer peripheral surface. By providing the abrading material along such surface the present tool can also be used to provide cutting by moving the tool laterally through the series of bores to be formed in the tooth root, as will hereinafter be explained.

It should be noted, that the diameter of the stem 22 need not correspond to the diameter of the shank. Specifically, the diameter of the stem 22 should be such as to fit into the bore provided into the tooth root, as will hereinafter be explained.

Referring now to FIGS. 5-8, there is shown a dental drill jig 50, which can be utilized in conjunction with the dental tool of FIG. 1 in the formation of a suitable contoured bore in a tooth root. The dental jig 50 includes an upper head block 52 from which depends a central cylindrical shaft 54. The head block is stepped, having a raised portion 56 and a lower portion 58. A first aperture 60 extends through the raised portion 56. A second aperture 62 extends through the lower portion 58.

Figure 8:
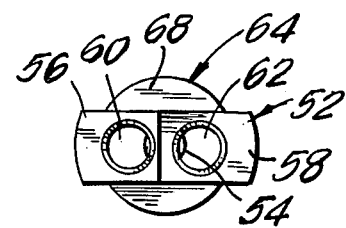
FIG. 8 is a top view of the dental jig shown in FIG. 6.
Figure 7:
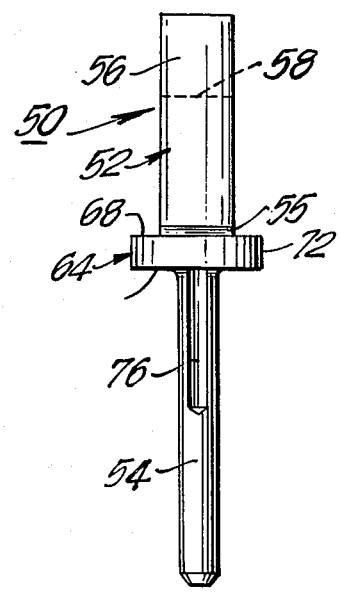
FIG. 7 is a side view of the dental jig shown in FIG. 6.
Figure 6:
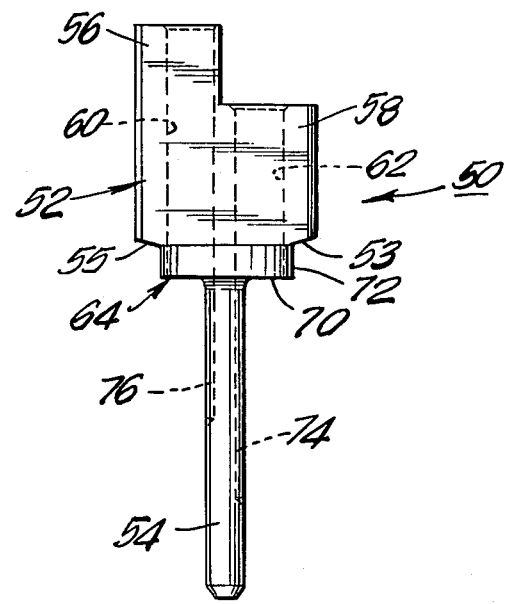
FIG. 6 is an elevational view of the dental jig shown in FIG. 5.

Interspaced between the head portion 52 and the shaft 54 is an annular flange 64 which extends outwardly beyond the width of the head block 52, as best seen in FIG. 8. The diameter of the shaft 54 will depend upon the size of the central bore pre-drilled in the tooth root. Likewise, the apertures 60 and 62 will depend on the size of the central bore. For a large central bore, the shaft will be larger than the apertures 60, 62 and accordingly, the diameter of the annular flange 64 will then intersect the apertures 60 and 62. However, for a smaller central bore, the shaft 54 will likewise be of smaller diameter. As shown, for a smaller diameter shaft, the apertures 60 and 62 approximate the size of the shaft. Accordingly, the diameter of the annular flange 64 is such that it extends slightly beyond the diametrically opposed ends of the apertures 60, 62 along the central axis 66 of the head block 52. The annular flange 64 includes an upper surface 68, a lower surface 70, and a cylindrical peripheral outer wall 72.

Both apertures 60 and 62 are parallel to each other, and likewise parallel to the central shaft 54. Both apertures extend downwardly through the flange 64 and project along the shaft 54, penetrating the shaft along a portion thereof as they extend therealong. The aperture 62 extends downwardly and continues a greater length along the shaft, as shown by the dotted lines 74. The aperture 60, continues along the shaft 54 for a lesser extent, as shown by the dotted line 76 in FIG. 6. & The entire length of the apertures 60, 62 are actually equal to each other. Specifically, the distance from the top surface of the lower portion 58 of the head block to the bottom end of the shaft cut out 74, is the same as the distance from the top surface of the raised portion 56 to the bottom edge, of the cut out portion 76 for the aperture 60. Thus, because of the stepped height arrangement of the head block 52, the aperture 62 extends downwardly along the shaft 54 by an additional amount from the end of the aperture 60. This additional amount being equal to the distance between the top surfaces of the raised portion 56 and the lower portion 58.

Figure 9:
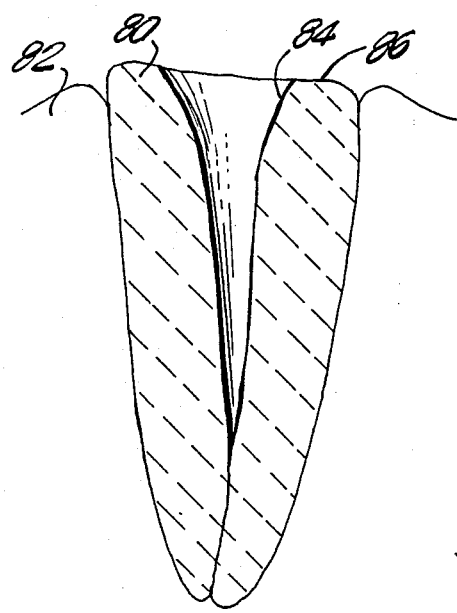
FIG. 9 shows a cross sectional view through a tooth root having an apical canal, on which a dental superstructure is to be fabricated.

The dental tool of FIG. 1 and the dental drill jig of FIG. 5 can be used in the fabrication of a superstructure onto a damaged devitalized tooth root as will hereinafter be described. FIG. 9 shows a tooth root 80 situated within a gum area 82 and having an apical canal 84 extending into the tooth root. The tooth root is initially prepared through the use of root canal procedures to devitalize the dentition. Typically, the upper surface 86 of the dentition will be rough, unfinished, and will not provide a flat surface. In the prior art, it was typical to cut down the upper surface in order to provide a level arrangement on which a drill jig could be placed and ultimately the tooth core can be secured. In doing so, however, healthy dentition was often destroyed. Additionally, by making the top of the tooth surface level, and ultimately securing a core directly thereto, the interface between the core and the tooth surface was unprotected and subject to shearing or loosening between the core and the tooth root occlusal surface.

Using the techniques and apparatus as hereinafter will be described, it is possible to place the core onto a level surface, and at the same time, avoid the necessity for destruction of excess of the healthy dentition at the irregular, angled surface of the tooth root. Furthermore, there will be provided a ledge of healthy dentition which will serve as a protection fence at interconnection between the core and the surface of the tooth root.

Figure 10:
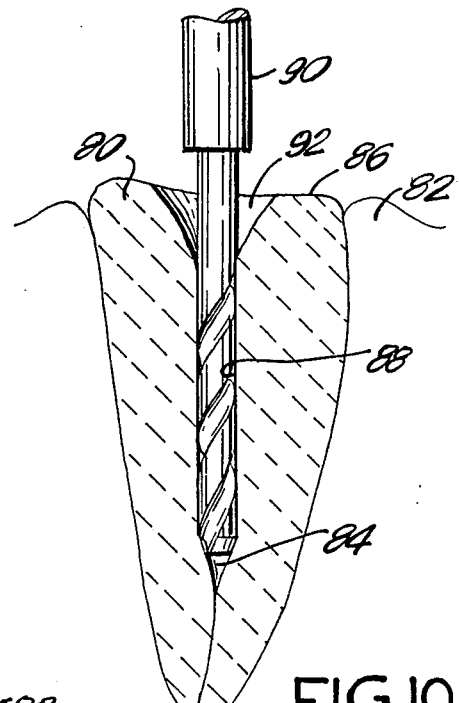
FIG. 10 is a view similar to that shown in FIG. 9 and showing a first step in the formation of a central bore in the tooth root.

In carrying out of the procedures of the present invention, as shown in FIG. 10, a central bore 88 is preformed coaxial with the apical canal 84 in the tooth root 80. A series of progressively larger drill bits 90 can be utilized to form the central bore 88, as is well known in the art.

Figure 11:
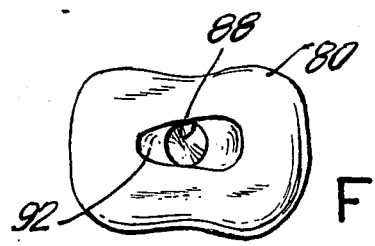
FIG. 11 is a top view of the tooth root of FIG. 10.

As best seen in FIGS. 10 and 11, the upper end of the canal has a flared mouth 92 which is substantially oval in cross sectional shape. Accordingly, the central bore 88 is not wide enough to extend the entire width of the mouth. As was heretofore explained, to make the central bore wide enough to cover the entire width of the flared mouth would cause destruction of an excessive amount of healthy dentition and weaken the tooth root. To use cement to fill in the space around a cylindrical post inserted in the bore has been found to permit weakening of the interconnection since the cement may of loosen over such a wide area. Accordingly, the solution suggested by the aforementioned U.S. Pat. No. 4,600,392 and incorporated within the Triax system, is to provide a contoured hole which proximates the shape of the apical canal, including its flared mouth. In doing so, a dental drill jig, as described in the aforementioned patent, would have been inserted into the bore prepared through the steps shown in FIGS. 10 and 11. In order to secure the positioning of the dental jig, however, a level surface would have been needed. Accordingly, the upper surface of the tooth root would have been completely leveled to secure the placement of the dental drill jig. This would have destroyed a lot of the healthy dentition which may be positioned angularly in an uneven manner across the upper surface of the tooth root.

Figure 12:
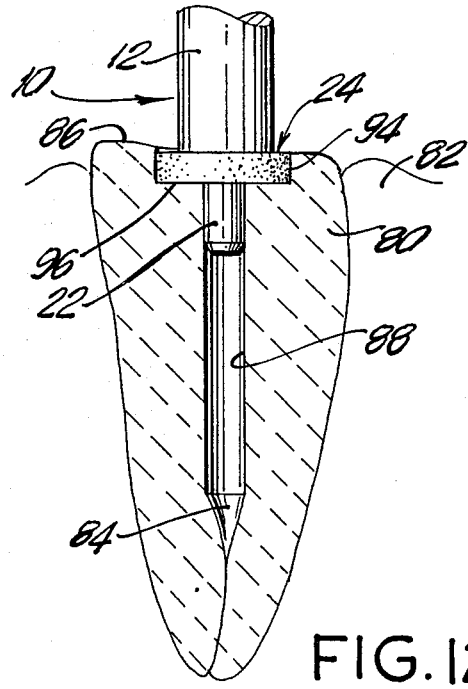
FIG. 12 shows a similar view to that shown in FIG. 10 with the insertion of the dental tool of FIG. 1, for the formation of a level counterbored recess at the mouth of the bore.

Referring now to FIG. 12, it will be noted, that the upper surface 86 of the tooth root 89 is not entirely leveled off. Instead, the dental tool 10, as shown in FIG. 1 is utilized to provide a level counterbore recess 92, at the mouth of the bore 88. The stem 22 is sized to approximate the size of the bore 88 and is inserted within the bore. The shank portion 12 is connected to the dental handpiece, or other rotating apparatus and is rotated whereby the abrading undersurface and peripheral outer surface of the projecting flange 24 will grind down and form a counterbore arrangement at the mouth of the bore 88. Since the undersurface of the flange 24 is substantially perpendicular to the stem 22, the bottom wall 96 of the counterbore recess 94 will be level and perpendicular to the bore 88.

Figure 5:
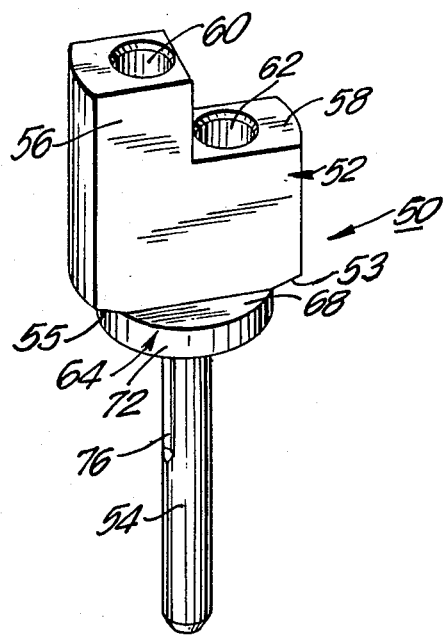
FIG. 5 is a perspective view of a dental drill jig for use in the formation of a contoured bore, the dental jig sitting into the counterbored recess formed by the dental tool of FIG. 1.
Figure 13:
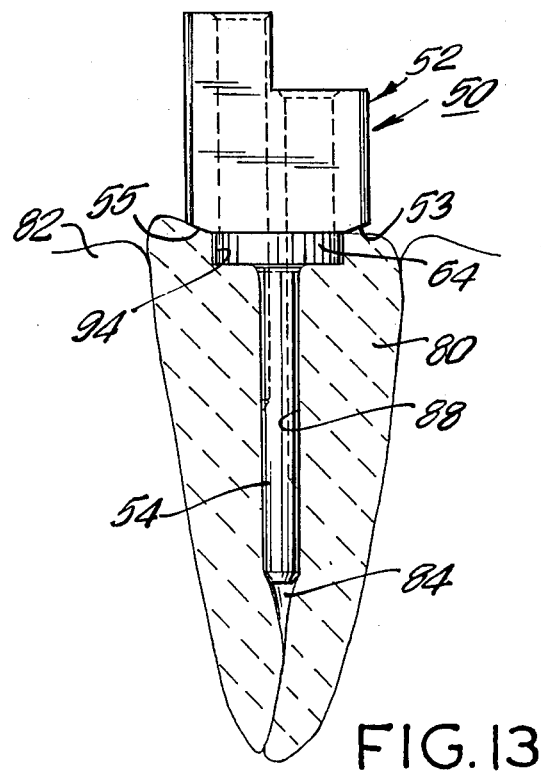
FIG. 13 is a view similar to that shown in FIG. 12 with the insertion of the dental jig shown in FIG. 5 suitably seated into the counterbored recess formed in FIG. 12.

The dental drill jig 50 of FIG. 5 is then inserted into the bore, as shown in FIG. 13. The stem 54 fits into the bore 88 and the enlarged annular flange 64 is sized as to snugly fit into the counterbore recess 94 at the mouth of the bore 88. The head portion 53 sits above the surface of the tooth. The slight angular undercuts 53, 55 are useful in spacing the head block 52 from any jagged edges or upturned angular shapes at the uncut surface of the tooth root 80. Because the flange 64 sits in the recess 94, the jig will remain secure in place and will not be subjected to lateral movement which might otherwise occur because of the wide flanged mouth.

Figure 14:
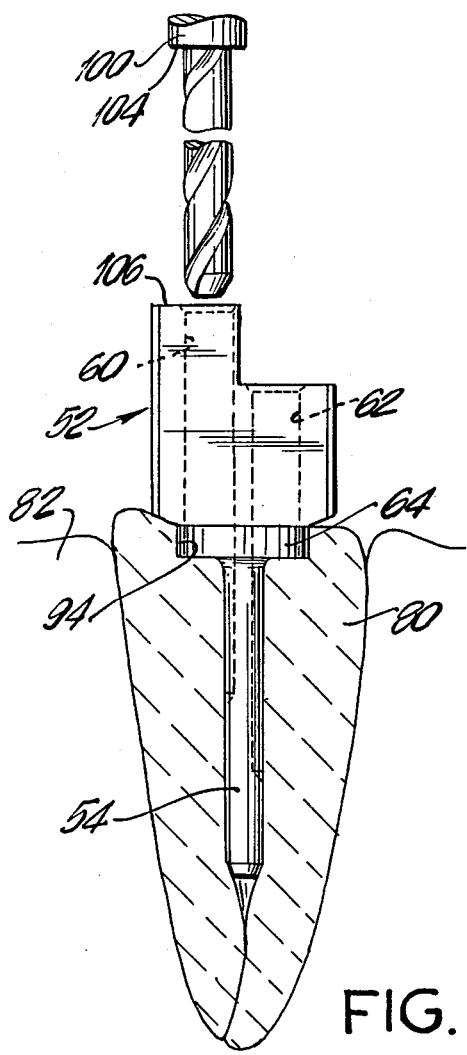
FIG. 14 is a view similar to that shown in FIG. 13 showing the use of the jig to form a first ancillary bore contiguous to the central bore in the formation of a contoured aperture in the tooth root.
Figure 15:
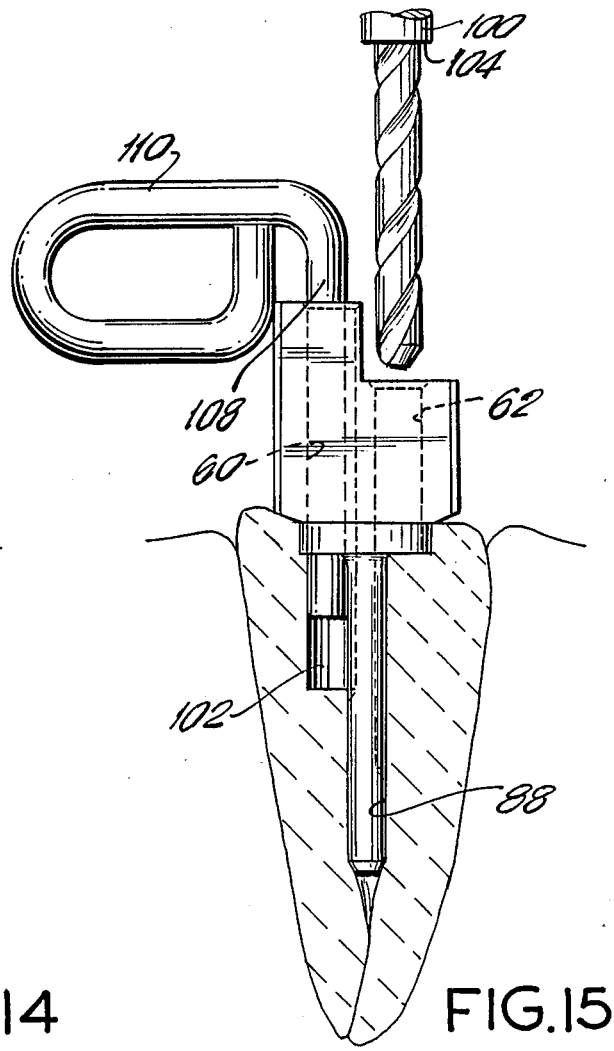
FIG. 15 is a next step in the formation of the contoured aperture in the tooth root and showing the formation of an opposing ancillary bore continguous with the central bore.

With the dental jig in place, as shown in FIG. 14, a dental drill bit 100 is inserted into one of the apertures, hereinshown as the aperture 60 and used to drill downward into the tooth root 80 to form a first ancillary bore 102 adjacent to and contiguous with the central bore 88. The drill can be sized so that the shoulder portion 104 abuts the upper surface 106 of the head block 52 when the proper depth of the ancillary bore 102 is reached.

After the first ancillary bore 102 is drilled, a suitable plug or pin 108, shown as having a hooked handle 110, is placed into the first ancillary bore 102 to prevent the drill jig from moving. The same drill bit 100 is then used to drill a second ancillary bore 112 in diametric opposition to the first ancillary bore 102 and likewise contiguous on the opposing side with the central bore 88. As heretofore explained, the same drill bit 100 can be utilized and will stop when the shoulder portion 104 hits the upper surface of the lower portion of the head block 52 and the depth of the second ancillary bore 112 will be appropriately formed.

Figure 16:
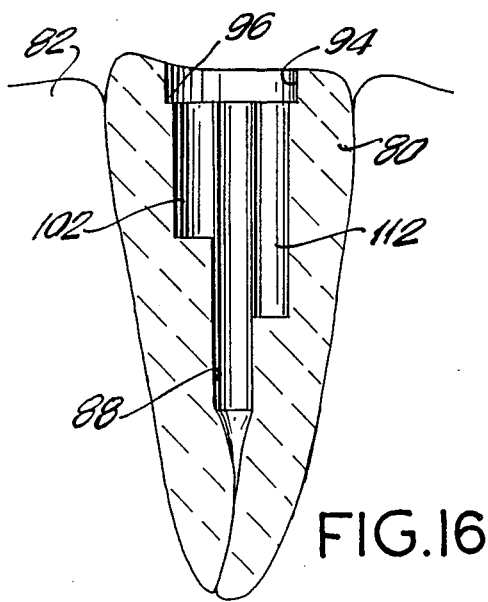
FIG. 16 shows the resultant contoured bore including the central bore and the ancillary bores, with the counterbored recess at the mouth of the central bore.
Figure 17:
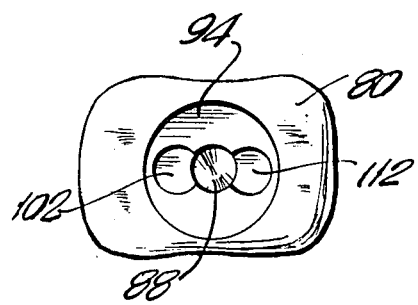
FIG. 17 is a top view of the tooth shown in FIG. 16.

As shown in FIG. 16 and 17, the resultant contoured, arrangement, in the tooth root 80 will include a central bore 88 with a pair of side ancillary bores 102, 112 whose total upper configuration approximates the oval shape of the canal at its upper mouth. At the same time, a limited amount of dentition is destroyed since the side ancillary bores do not extend the full depth of the tooth root. The counterbored recess 94 is formed around the central bore and serves to position the drill jig in place on a level surface and seat it properly without the necessity of destroying the entire upper surface of the tooth root. As shown in FIG. 17, for the size of the bores shown, the counterbore extends beyond the opposing maximum axial distance between the opposing ancillary bores 102 and 112. As will hereinafter be explained, for other sized bores the counterbore could be such that it would intersect the ancillary bores.

As shown in FIG. 18, the dental tool 10 of FIG. 1 can be further utilized. This time, it is inserted first into one ancillary bore 102, as shown in FIG. 18, and subsequently into the opposing ancillary bore 112. In each case, the shank portion 12 will be rotated so that the undersurface and the peripheral outer surface of the enlarged flange 24 will cut suitable counterbore recesses around each of the ancillary bores 102, 112.

As best shown in FIG. 20, the total composite arrangement of the three recesses will form a substantially oval channel 114 below the surface of the tooth root 80. This channel will have a substantially flat base wall 116 to provide a level surface on which a dental core can be seated. The slight projections 118 at the intersection between the three circular counterbored recesses can be cut away to provide a smooth oval channel corresponding in shape to the bottom of the core. The tool of FIGS. 1-4 can be used for this purpose by laterally moving the tool through the three bores and by using the abrading peripheral edge to smooth out the edges.

As shown in FIG. 22, where the central bore 150 is larger, the two ancillary bores 152, 154 could be smaller. The central counterbore 156 would tend to intersect the ancillary bores 152, 154. The counterbores 158, 160 would be formed around the ancillary bores 152, 154. These could be smooth out to provide a substantially oval configuration.

As shown in FIG. 21, a suitable post and core shown generally at 120, can now be cemented in place. The post portion 122 can be of the Triax configuration having a central post 124 with side ribs 126, 128 which suitably fit into the contoured bore formed in the tooth including the central bore and the ancillary bores. The core 130 will have a flat bottom 132 which will sit in the flat level bottom 116 of the substantially oval shaped channel 114. It will be appreciated, that the side portions 134, 136 of the upper part of the tooth root 80 have not been cut away and serve to provide a peripheral ledge or rim which will protect the interface between the core and the tooth root. Furthermore, the core will be secured in place on a level surface which is perpendicular to its post and will be protected by the outer periphery of the tooth. The dental post and core is secured in place by means of cement 138. An appropriate crown or superstructure 140 is then fabricated and secured onto the core by means of additional cement 142.

Through the use of the present method, it is now possible to utilize a pre-case post and core which is substantially uniform for all anterior teeth and posterior teeth. Since the contoured bores will be of standard size and configuration, the post can be precast to these standard sizes. Similarly, the core can be precast in sizes as part of an integral structure with the post since it will fit into the sized channel which can be made of substantially standard size regardless of the outer peripheral shape of the tooth root.

The size of the bore that is pre-drilled in the center of the tooth will vary in accordance with the size and type of the tooth. The dental jig as shown in FIG. 5 and the dental tool as shown in FIG. 1 will likewise vary in size. Specifically, the dental jig will have its central shaft of a size to correspond to the size of the central bore. Likewise, the stem projecting from the dental tool will also correspond to the central bore.

The side apertures in the dental jig can have a small and large size even though the central bore can vary in specific increments. An additional dental tool, as shown in FIG. 1, would be used for the large or small ancillary bores that are drilled.

A suitable kit could be provided which includes the varied sized dental drill jigs with corresponding sized dental tools for making the counterbore recesses. Two additional dental tools would be included for the large and small ancillary bores.

As an alternative, a single dental tool can be utilized and the stems could be replaceable into the tool. Such could be provided by screwing into the stems with the stems being of diffeent sizes, as needed. These could be provided with a flat on one side for orienting it properly and using a suitable locking arrangement, such as a lock screw which could be provided to lock the stem in place.

The stem can be of varied length as long as it fits into the bores in which it is being used. It can be spring loaded so that pressure is provided to push down the dental tool as it grinds the channel.

The dental post and core shown in FIG. 21 as precast, can actually be of different metal for the post and a different metal for the core. The upper part could also be a ceramic or composite and the post of a different material. However, these can be preformed and can be made precast before use and then selected to fit into the particular sized tooth and bores that are drilled.

There has been described heretofore the best embodiment of the invention presently contemplated. However, it is to be understood that various changes and modifications may be made thereto without departing from the spirit of the invention.

What is claimed is:

1. A dental tool for leveling at least a portion of the surface of a tooth root having a pre-drilled center bore in preparation for receiving a dental post and core during the fabrication of a superstructure on the tooth root, the tool comprising a rigid elongated cylindrical shank portion, coupling means at one end thereof for securement into a rotating apparatus, a cylindrical rigid stem projecting from another end thereof, an enlarged annular collar intermediate the stem and shank portion, said collar having an undersurface facing said stem and an outer peripheral wall, and abrasion means on said undersurface and said outer peripheral wall, said stem being constructed for insertion into said pre-drilled center bore and positioning said collar over said bore, whereby with the stem inserted in the tooth bore, rotation of the dental tool will provide a level bottomed counterbore at a mouth of the bore and a contoured rim about the counterbore.

2. A dental tool as in claim 1, wherein said undersurface is perpendicular to said stem, whereby the counterbore will be perpendicular to the axis of the post to be inserted into the tooth bore.

3. A dental tool as in claim 1, wherein said collar has an annular shape including a circular outer wall, and including abrasion means on said outer wall.

4. A dental tool as in claim 1, wherein said collar has a frustroconical shape.

5. A dental tool as in claim 1, wherein said shank and stem are coaxial.

6. A dental tool as in claim 1, wherein said coupling means comprise a cylindrical head portion, a flat on one side of said head portion terminating in a lower ledge, and an annular reduced diameter neck around said head portion and above said ledge portion.

7. A dental tool as in claim 1, wherein said stem is sized to partially enter the bore.

8. A dental tool as in claim 1, wherein said stem is replaceable in said shank portion.

9. A dental drill jig for use in making bores in a tooth root for receiving a post and core in the fabrication of a superstructure on the tooth root, the jig comprising a head block, a cylindrical stem depending from the head block for insertion into a pre-drilled central bore in the tooth root, a projecting flange interconnecting the stem and the head block for positioning in a counterbore recess at a mouth of the central bore, and a pair of spaced apart apertures parallel to said stem and extending through said head block and said flange, and penetrating along at least a portion of said stem, said apertures receiving drill bits for the formation of ancillary bores in the root flanking the pre-drilled bore.

10. A dental drill jig as in claim 9, wherein the undersurface of the flange is planar and perpendicular to the stem.

11. A dental drill jig as in claim 9, wherein the flange is annular and extends beyond the thickness of the head block.

12. A dental drill jig as in claim 9, wherein said head block is stepped to form a raised surface and a lower surface, each of said apertures being respectively in said raised and lower surfaces.

13. A dental drill jig as in claim 12, wherein said apertures are in diametric opposition with respect to said stem.

14. A dental drill jig as in claim 9, wherein one aperture extends along said stem for a greater length than the other aperture.

15. A dental drill jig as in claim 9, wherein said flange is annular in shape.

16. A dental drill jig as in claim 9, wherein the respective diameter of said apertures are less than the diameter of said stem.

17. A dental drill jig as in claim 16, wherein the diameter of said apertures are the same.

18. In combination, a dental tool for forming a recessed planar surface on a tooth root having a center bore pre-drilled into the tooth root, and a dental drill jig insertable into the recessed planar surface for use in forming an ancillary bore contiguous with the center bore, wherein a dental post and core will be positioned for retaining a dental restoration on the tooth root, said dental tool comprising:
   a shank insertable into an instrument for rotational movement;
   a depending stem extending from the shank for insertion into the center bore; and
   a flanged abrading surface annularly projecting from an upper end of the stem for forming a recessed surface on the tooth root;
   the dental drill jig comprising:
   a head block;
   a depending shaft extending from said head block for insertion into said center bore;
   a flanged member annularly projecting from an upper end of the shaft for seating into the recessed surface in the tooth root; and
   at least one aperture passing through the head block and through the flanged member and extending along at least a portion of the shaft, through which a drill can pass to form an ancillary bore.

19. The combination as in claim 18, wherein the flanged surface on the tool and the flanged member on the jig substantially correspond in shape and size.

20. The combination as in claim 19, wherein the flanged surface is perpendicular to the stem and the flanged member is perpendicular to the shaft, whereby the recessed surface is perpendicular to the bore.

21. The combination as in claim 19, wherein the flanged surface and the flanged member are circular.

22. A method of preparing a tooth root for receiving a post and core for the retention of a dental restoration on the tooth root, the method comprising the steps of:
   (a) forming a central bore in the canal of a tooth root;
   (b) providing a dental tool having an insertion stem and an abrading flange and inserting the stem of the dental tool into the bore so that said flange is positioned over said central bore and rotating the tool such that the abrading flange of the tool cuts a counterbore recess with a level bottom wall around a mouth of the central bore; and
   (c) placing a post and core onto the tooth root with the post inserted in the central bore and the core secured in the counterbore recess.

23. The method as in claim 22, wherein the bottom wall is perpendicular to the central bore.

24. The method as in claim 22, and further comprising the steps of:
   (a) inserting a jig into the tooth root with a shaft of the jig inserted into the central bore, an enlarged flange inserted into the counterbore recess, and a headblock positioned above a tooth surface;
   (b) using the jig for drilling at least one ancillary bore into the tooth root, parallel to and contiguous with the central bore;
   (c) inserting the dental tool into the ancillary bore to cut a counterbore recess about a mouth of the ancillary bore, the recess merging into a continuous channel in the tooth root surface.

25. The method as in claim 24, and further comprising the steps of drilling two ancillary bores in diametric opposition to the central bore, each bore having its own counterbore recess, whereby the resulting channel compositely approximates the oval shape of a core.

26. A method of preparing a tooth root for receiving a post and core for the retention of a dental restoration on the tooth root, the method comprising the steps of:
   (a) forming a central bore in the canal of a tooth root;
   (b) inserting a stem of the dental tool into the bore and rotating the tool such that an abrading flange of the tool cuts a counterbore recess with a level bottom wall around a mouth of the central bore;
   (c) inserting a jig into the tooth root with a shaft of the jig inserted into the central bore, an enlarged flange inserted into the counterbore recess, and a headblock positioned above a tooth surface;
   (d) using the jig for drilling at least one ancillary bore into the tooth root, parallel to and contiguous with the central bore;
   (e) inserting the dental tool into the ancillary bore to cut a counterbore recess about a mouth of the ancillary bore, the recess merging into a continuous channel in the tooth root surface;
   (f) placing a post and core onto the tooth root with the post inserted in the central bore and the core secured in the counterbore recess.

27. The method of claim 26, and further comprising the steps of drilling two ancillary bores in diametric opposition to the central bore, each bore having its own counterbore recess, whereby the resulting channel compositely approximates the oval shape of a core.

* * * * *